United States Patent [19]

Chan

[11] Patent Number: 5,312,832

[45] Date of Patent: May 17, 1994

[54] OCULAR HYPOTENSIVE 2-DECARBOXYL-2-ACYLTHIOALKYL PROSTAGLANDIN DERIVATIVES

[75] Inventor: Ming F. Chan, Gurnee, Ill.

[73] Assignee: Allergan, Inc., Irvine, Calif.

[21] Appl. No.: 702,220

[22] Filed: May 17, 1991

[51] Int. Cl.$^5$ ............................................. A61K 31/557
[52] U.S. Cl. ...................................... 524/513; 558/252
[58] Field of Search ......................... 560/231; 514/513; 558/252

[56] References Cited

U.S. PATENT DOCUMENTS 4,256,745  3/1981  Skuballa .............................. 568/838

FOREIGN PATENT DOCUMENTS 0051284   5/1982  European Pat. Off. .
7834747   3/1978  Japan .................................. 560/121
WO91/19490 12/1991 PCT Int'l Appl. .

Primary Examiner—Robert Gerstl
Attorney, Agent, or Firm—Robert J. Baran; Howard R. Lambert; Martin A. Voet

[57] ABSTRACT

The present invention relates to 2-decarboxyl-2-acylthioalkyl prostaglandins that are potent ocular hypotentives, and are particularly suitable for the management of glaucoma.

4 Claims, No Drawings

OCULAR HYPOTENSIVE 2-DECARBOXYL-2-ACYLTHIOALKYL PROSTAGLANDIN DERIVATIVES

FIELD OF THE INVENTION

The present invention relates to 2-decarboxyl-2-acylthioalkyl prostaglandins that are potent ocular hypotentives, and are particularly suitable for the management of glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which has the following structural formula:

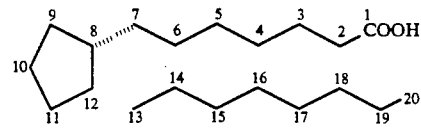

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ (PGE$_1$), prostaglandin $E_2$ (PGE$_2$)], and on the configuration of the substituents on the alicyclic ring indicated by $\alpha$ or $\beta$ [e.g. prostaglandin $F_{2\alpha}$ (PGF$_{2\alpha}$)].

Prostaglandins were earlier regarded as potent ocular hypertensives, however, evidence accumulated in the last decade shows that some protaglandins are highly effective ocular hypotensive agents, and are ideally suited for the long-term medical management of glaucoma (see, for example, Bito, L. Z. *Biological Protection With Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include PGF$_{2\alpha}$, PGF$_{1\alpha}$, PGE$_2$, and certain lipid-soluble esters, such as $C_1$ to $C_2$ alkyl esters, e.g. 1-isopropyl ester, of such compounds.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28 (suppl), 284 (1987)].

The isopropyl ester of PGF$_{2\alpha}$ has been shown to have significantly greater hypotensive potency than the parent compound, presumably as a result of its more effective penetration through the cornea. In 1987 this compound was described as "the most potent ocular hypotensive agent ever reported" [see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF$_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl PGF$_{2\alpha}$. Intraocular pressure reducing 15-acyl prostaglandins are disclosed in the co-pending application U.S. Ser. No. 357,394 (filed 25 May 1989). Similarly, 11,15- 9,15- and 9,11-diesters of prostaglandins, for example 11,15-dipivaloyl PGF$_{2\alpha}$ are known to have ocular hypotensive activity. See the co-pending patent applications U.S. Ser. Nos. 385,645, 386,312 and 386,834 (all filed 27 Jul. 1989). PGF 1-alcohols are disclosed in the co-pending application U.S. Ser. No. 07/538,204, filed 14 Jun. 1990. The disclosures of all of these patent applications are hereby expressly incorporated by reference.

Prostaglandin-like compounds, including 2-decarboxyl-2-thiomethyl $PGF_{2\alpha}$, and their preparation are disclosed in the Japanese Kokai JP 53/34747 as oral contraceptives.

SUMMARY OF THE INVENTION

The present invention relates to new 2-decarboxyl-2-acylthioalkyl prostaglandin derivatives.

It has been found that these compounds are potent ocular hypotensive agents and are particularly useful in the treatment of diseases of the eye characterized by increased intraocular pressure, such as glaucoma. The ocular hypotensive activity of the 2-decarboxyl-2-acylthioalkyl prostaglandins is entirely unexpected, especially since the structurally closest known compound, 2-decarboxyl-2-mercapto methyl $PgF_{2\alpha}$ is substantially ineffective in lowering intraocular pressure.

It has further been found that the compounds of the present invention cause significantly less ocular surface hyperemia than their respective parent PG compounds.

In one aspect, the present invention relates to 2-decarboxyl-2-acylthioalkyl prostaglandin derivatives of the formula (I)

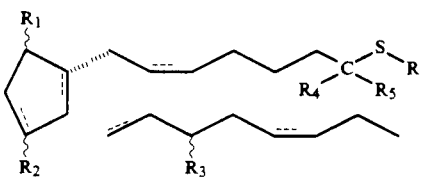

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; R is an acyl group; one of $R_1$ and $R_2$ is =O, —OH or an —O(CO)$R_6$ group, and the other one is —OH or an —O(CO)$R_6$ group or $R_1$ is =O and $R_2$ is H; $R_3$ is —OH or —O(CO)$R_6$; one of $R_4$ and $R_5$ is hydrogen and the other one is hydrogen or an alkyl group having from 1 to about 4 carbon atoms $R_6$ is a saturated or unsaturated acyclic hydrocarbon group having from 1 to about 20 carbon atoms, or —(CH$_2$)$_n$R$_7$ wherein n is 0–10, and $R_7$ is an aliphatic ring from about 3 to about 7 carbon atoms, or an aromatic or heteroaromatic ring; and to pharmaceutically acceptable salts of these compounds.

In another aspect, the present invention concerns pharmaceutical compositions for the treatment of ocular hypertension, comprising an amount sufficient to treat ocular hypertension of a compound of formula (I) as hereinabove defined, or a pharmaceutically acceptable salt thereof, usually in admixture with a non-toxic, ophthalmically acceptable carrier.

In a further aspect, the invention concerns a method of treating ocular hypertension which comprises applying to the eye an amount sufficient to treat ocular hypertension of a compound of formula (I), wherein the various symbols and substituents are as hereinabove defined.

In a still further aspect, the invention concerns ophthalmic solutions for the treatment of ocular hypertension, comprising an amount sufficient to treat ocular hypertension of a compound of formula (I), in admixture with a non-toxic, ophthalmically acceptable liquid vehicle. The ophthalmic solutions are usually packaged in a container suitable for metered application.

In an other aspect, the present invention relates to a pharmaceutical product, comprising a container adapted to dispense its contents in metered form; and an ophthalmic solution therein, as hereinabove defined.

DETAILED DESCRIPTION OF THE INVENTION

The present invention relates to novel 2-decarboxyl-2-acylthioalkyl prostaglandin derivatives that are useful as ocular hypotensives. These prostaglandin derivatives are encompassed by the following general formula (I)

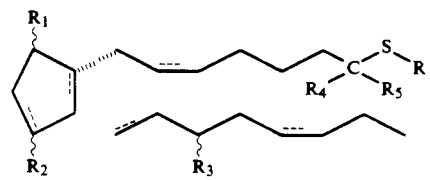

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; R is an acyl group; one of $R_1$ and $R_2$ is =O, —OH or an —O(CO)$R_6$ group, and the other one is —OH or an —O(CO)$R_6$ group or $R_1$ is =O and $R_2$ is H; $R_3$ is —OH or —O(CO)$R_6$ one of $R_4$ and $R_5$ is hydrogen and the other one is hydrogen or an alkyl group having from 1 to about 4 carbon atoms $R_6$ is a saturated or unsaturated acyclic hydrocarbon group having from 1 to about 20 carbon atoms, or —(CH$_2$)$_n$R$_7$ wherein n is 0–10, and $R_7$ is an aliphatic ring from about 3 to about 7 carbon atoms, or an aromatic or heteroaromatic ring.

The above formula includes 2-decarboxyl-2-acylthioalkyl derivatives of prostaglandins of the F, D, E, A and B series.

A preferred group of the compounds of the present invention is encompassed by the following formula (II)

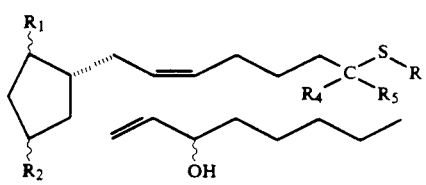

wherein $R_1/R_2$ is —OH/—OH, =O/—OH, —OH/=O and the 9- and/or 11- and/or 15-esters of these compounds. This definition includes PGF$_2$, PGE$_2$ and PGD$_2$ derivatives.

Particularly preferred are the PGF$_{2\alpha}$ derivatives of the formula (III)

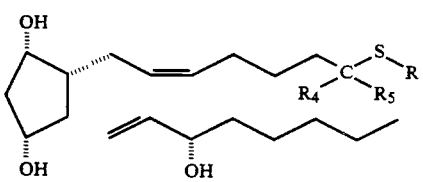

and their 9- and/or 11- and/or 15-esters.

In all of the above formulae, as well as in those provided hereinafter, the dotted lines on bonds between carbons 5 and 6 (C-5); between carbons 8 and 12 (C-8); between carbons 10 and 11 (C-10); between carbons 13 and 14 (C-13), and between carbons 17 and 18 (C-17) indicate a single or a double bond which can be in the cis or trans configuration. If two solid lines are used, that indicates a specific configuration for that double bond. Hatched lines at positions C-9, C-11 and C-15 indicate the α configuration. If one were to draw the β configuration, a solid triangular line would be used.

The naturally occurring stereochemistry of $PGF_{2\alpha}$ includes the C-9, C-11, and C-15 hydroxy groups in the α configuration. In the compounds used in accordance with the present invention, however, prostaglandins having the C-9 or C-11 or C-15 substituents in β configuration are also contemplated. As hereinabove mentioned, in all formulas provided herein broken line attachments to the cyclopentane ring indicate substituents in the αconfiguration. Thickened solid line attachments to the cyclopentane ring indicate substituents in the β configuration. For instance, 9β-PGF compounds have the same structure as $PGF_\alpha$ compounds, except that the hydroxyl at the C-9 position is in the β configuration. Also, the broken line attachment of the hydroxyl group or other substituent to the C-11 and C-15 carbon atoms signifies the α configuration; therefore, compounds with the epi configuration for the hydroxyl group at C-15 are designated by using 15β and if there is no indication of the β configuration, the configuration is assumed α.

The term "acyl" is used to refer to a radical derived from a carboxylic acid by removal of the hydroxyl portion of the carboxyl group. Such groups may be represented by the formula A—CO—, wherein A is an aliphatic or aromatic, saturated or unsaturated hydrocarbon group, each of which may be substituted or unsubstituted. The term "aliphatic hydrocarbon group" is used to refer to straight of branched chained, saturated or unsaturated acyclic hydrocarbon groups or may include a cyclic component (alicyclic hydrocarbon group). The acyclic aliphatic hydrocarbon groups contemplated in the definition of A preferably have from one to about 6, preferably one to about 4 carbon atoms. Such groups include straight or branched chained alkyl, alkenyl and alkinyl groups of appropriate lengths, and preferably are alkyl, e.g. methyl, ethyl, propyl, butyl, pentyl, or hexyl, or an isomeric form thereof. The the alicyclic hydrocarbon groups preferably have a saturated or unsaturated aliphatic ring of about 3 to about 7 carbon atoms. This ring may be attached to an acyclic aliphatic hydrocarbon moiety as hereinabove defined, which preferably has up to about 4 carbon atoms. A as an aromatic hydrocarbon group preferably is aryl, e.g. phenyl, or aralkyl, e.g. benzyl, but also includes heteroaromatic rings, containing oxygen and/or nitrogen and/or sulfur as a heteroatom. In all of the above definitions, the acyl group may carry one or more identical or different substituents, preferably selected from halogen (e.g. chlorine, bromine, iodine), nitro, hydroxy, amino, alkoxy (e.g. methoxy or ethoxy), alkyl (e.g. methyl, ethyl), etc. In the most preferred compounds, the acyl group is derived from a straight or branched chained acyclic aliphatic carboxylic acid, preferably alkylcarboxylic acid having from 1 to about 6, preferably 1 to about 4 carbon atoms in the alkyl moiety.

In the definition of $R_6$, the term "saturated or unsaturated acyclic hydrocarbon group" is used ro refer to straight or branched chained, saturated or unsaturated hydrocarbon groups of appropriate lengths. Such groups include alkyl, alkenyl and alkinyl groups, as hereinabove defined.

In the definition of $R_4$ and $R_5$, the alkyl group preferably has 1 or 2 carbon atoms, and more preferably is methyl.

The definition of $R_6$ may include a cyclic component, $(CH_2)_n R_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen and/or nitrogen and/or sulfur as a heteroatom. Preferably n is 0–4.

Of the compounds disclosed in the present invention, preferred are the $PGF_{2\alpha}$ derivatives encompassed by the formula (III), and their 9- and/or 11- and/or 15-esters, as defined with respect to the symbols $R_1$, $R_2$ and $R_3$ in formula (I).

Particulary preferred are the $PGF_{2\alpha}$ derivatives in which R is an acyclic aliphatic acyl group of up to about 7 carbon atoms, preferably containing an alkyl moiety of 1 to about 6, preferably 1 to about 4, most preferably 1 or 2 carbon atoms, and $R_4$ and $R_5$ are both hydrogen, or one of them is hydrogen and the other one is methyl. In the most preferred compounds, $R_4$ and $R_5$ are both hydrogen.

A pharmaceutically acceptable salt of the compounds according to the present invention is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

The new compounds of the present invention can be conveniently prepared from the 2-decarboxyl-2-hydroxyalkyl prostaglandins ("prostan-1-ols") disclosed in the U.S. Pat. No. 4,256,745, and in our co-pending application U.S. Ser. No. 07/538,204 (filed 14 Jun. 1990), the content of which is hereby expressly incorporated by reference, or from structurally analogous compounds.

From these starting compounds, the acyl compounds of the present invention can, for example, be prepared as described in Example 1 and illustrated in the attached Reaction Scheme. Other compounds may be prepared by similar reactions well known to those skilled in the art.

In general, all of the prostaglandin hydroxyls are protected with groups which are not subject to reduction and are readily removed, such as tetrahydropyranyl (THP) groups. The carboxylic acid can then be esterified and reduced or the acid reduced directly with lithium aluminium hydride or related reagents. The alcohol product obtained can be converted to a compound containing a leaving group, such as mesylate, tosylate or halide. Commonly this transformation is effected with mesyl chloride or tosyl chloride, and a base. Displacement of the mesylate obtained with an alkali metal salt of a thioester in a polar solvent such as dimethyl formamide (DMF) affords a protected product. Removal of the protecting groups with acid catalysis affords a compound, in which $R_4$ and $R_5$ are both hydrogen. To prepare compounds, in which one of $R_4$ and $R_5$ is hydrogen, and the other one is lower alkyl, preferably methyl, the alcohol obtained from acid or ester reduction is oxidized to an aldehyde, for example by chromium trioxide/pyridine or any other oxidants commonly used in this type of reactions. This aldehyde is then reacted with a suitable organometallic compound, such as MeMgX or MeLi (X is halogen), to provide a secondary alcohol at C-1 of the prostaglandin. This secondary alcohol can be converted into the desired product by the same sequence of reactions as outlined above, including formation of a leaving group, displacement with alkali thioester and removal of the protecting groups.

Alternatively, the compounds can be prepared from the corresponding mercaptan compounds. Acylation of a mercaptan in the presence of alcohols can be accomplished with an acid chloride or acid anhydride using a weak base (e.g. bicarbonate) or under neutral conditions. The hydroxyl groups in the 9- and/or 11- and/or 15-positions of the compounds according to the present invention can be acylated by method well known in the art, including those disclosed in the co-pending applications U.S. Ser. Nos. 386,835, 357,394, 385,645, 386,312, and 386,834.

Pharmaceutical compositions containing the novel compounds of the present invention as an active ingredient, may be prepared by combining a therapeutically effective amount of at least one compound according to the present invention, or a pharmaceutically acceptable acid addition salt thereof, with conventional ophthalmically acceptable pharmaceutical excipients. The therapeutically efficient amount typically is between about 0.0001 and about 5% (w/v), preferably about 0.001 to about 1.0% (w/v) in liquid formulations. A typical dose is one drop into the effected eye up to about 6-times, preferably up to about 4-times a day.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

EXAMPLE 1

Preparation of 2-decarboxyl-2-acetylthiomethyl $PGF_{2\alpha}$ $PGF_{2\alpha}$ methyl ester (prepared from $PGF_{2\alpha}$ and diazomethane, 240 mg, 0.57 mmol), was dissolved in $CH_2Cl_2$ (0.58 ml). 1,2-Dihydro-3H-pyran (0.52 ml, 5.7 mmol) was added followed by pyridinium tosylate (14 mg, 0.06 mmol). The reaction was stirred at 25° C. for 23 h and quenched with 10% citric acid. After being extracted into ethyl acetate, the crude product solution was washed with saturated sodium bicarbonate and brine, dried over magnesium sulfate and concentrated to give 387 mg of the crude $PGF_{2\alpha}$ methyl ester, 9,11,15-tris(THP) ether.

A 1.0M solution of diisobutylaluminum hydride in methylene chloride (1.7 ml, 1.7 mmol) was added at −78° C. to the crude product (353 mg, 0.56 mmol) obtained above. The resulting solution was stirred at 0° C. for 1.5 h and worked up by the addition of a saturated solution of Rochelle salt. The mixture was extracted three times with ethyl acetate. The organic extract was washed with brine and dried over magnesium sulfate. The solvent was evaporated to give 333 mg of crude product which was chromatographed over silica gel (40–50% ethyl acetate in hexanes) to give 243 mg pure 2-decarboxyl-2-(hydroxymethyl) PGF$_{2\alpha}$ 9,11,15-tris(THP) ether.

2-decarboxyl-2-(hydroxymethyl) PGF$_{2\alpha}$ 9,11,15-tris(THP) ether from above (243 mg, 0.411 mmol) and triethylamine (86 μl, 0.62 mmol) were dissolved in methylene chloride (2 ml) and cooled to 0° C. To the above solution was added dropwise over about 5 minutes methanesulfonyl chloride (35 μl, 0.45 mmol). The solution was stirred at 0° C. for 15 min and worked up by addition of 10% citric acid. The crude reaction mixture was extracted with methylene chloride and the extracts were washed with saturated sodium bicarbonate and brine. The organic phase was dried over anhydrous magnesium sulfate and concentrated to give 244 mg of 2-decarboxyl-2-mesyloxymethyl PGF$_{2\alpha}$ 9,11,15-tris (THP) ether.

The 2-decarboxyl-2-mesyloxymethyl compound (87 mg, 0.13 mmol) and potassium thioacetate (30 mg, 0.26 mmol) were dissolved in DMF (0.13 ml) and stirred at 25° C. for 2 h. The solution turned into a thick red mixture which was diluted with DMF (0.15 ml) and stirring was continued for a further 24 h. The reaction mixture was diluted with water and extracted with ethyl acetate to give the crude product which was purified by column chromatography (silica gel, 20% EtOAc in hexanes, R$_f$0.22) to give 47 mg pure 2-decarboxyl-2-acetylthiomethyl compound. Deprotection of the THP groups was achieved with pyridinium tosylate in methanol. Pure 2-decarboxyl-2-acetylthiomethyl-prostaglandin F$_{2\alpha}$ was isolated from chromatography on silica gel (80% EtOAc in hexanes, R$_f$0.14), yield 11 mg (40%).

$^1$H NMR (300 MHz, CDCl$_3$) δ5.52 (2H, ABX, J$_{AB}$=15, J$_{AS}$=6, J$_{BX}$=7.5 HZ), 5.38(2H, complex AB), 4.18(1H, t, J=4 Hz), 4.06(1H, q, J=6.5 Hz), 3.95(1H, m), 2.85(2H, t, J=7.3 Hz), 2.30(3H, s), 1.2–2.4(23H, m), 0.88 ppm (3H, t, J=5 Hz);

$^{13}$C NMR (75 MHz, CDCl$_3$): δ1.96.24, 135.37, 132.81, 130.37, 128.36, 77.87, 73.14, 72.88, 55.82, 50.15, 42.78, 37.23, 31.75, 30.66, 29.09, 28.93, 28.63, 26.67, 25.63, 25.23, 22.64, 14.06 ppm, IR (CHCl$_3$):3200–3600, 1690, 980, 940 cm$^{-1}$; MS (EI, TMS derivative):m/z 614.6(M$_+$, 1.0%). 453(12), 217(12), 191(38), 173(19), 147(17), 129(15), 75(20), 73(100);

HRMS (EI, TMS derivative):calculated for C$_{31}$H$_{62}$SO$_4$Si$_3$: 614.3675, found:614.3676.

EXAMPLE 2

Intraocular Pressure Reducing Activity

Experimental quantities of 2-decarboxyl-2-acetylthiomethyl PGF$_{2\alpha}$ were prepared in an ophthalmic formulation containing 0.1% polysorbate (Tween 80)—10 mM TRIS. One eye of each experimental animal was treated by applying one 25 μl drop of the drug formulation to the ocular surface, the contralateral eye received 25 μl of vehicle as a control. Intraocular pressure was measured by applanation pneumatonometry immediately before drug administration and at subsequent, predetermined times thereafter. New Zealand albino/dutch belted cross rabbits were employed as experimental animals.

Ocular surface hyperemia was assessed by observation at predetermined times after drug administration and is described as either present or absent.

The results obtained are shown in Table I.

The intraocular pressure reducing activity of the corresponding 2-decarboxyl-2-thiomethyl-compound, was determined under analogous conditions, and the results obtained are shown in Table II.

TABLE I

| PROSTANOID | (DOSE %) | 0 | 1.0 | 2.0 | 3.0 | 4.0 | 6.0 |
|---|---|---|---|---|---|---|---|
| | | EFFECT ON INTRAOCULAR PRESSURE (mmHg) AT PREDETERMINED TIMES POST-ADMINISTRATION | | | | | |
| 2-Decarboxyl-2-acetylthiomethyl | 0.01% PGF2$_a$ | — | −2.0 | −2.4** | −1.4* | −1.25 | −0.7 |
| 2-Decarboxyl-2-acetylthiomethyl | 0.1% PGF2$_a$ | — | −3.2* | −6.7** | −2.7 | −5.2** | −4.0** |
| | | % ANIMALS EXHIBITING OCULAR SURFACE HYPEREMIA | | | | | |
| 2-Decarboxyl-2-acetylthiomethyl | 0.01% PGF2$_a$ | — | 50 | 0 | 12.5 | 12.5 | 0 |
| 2-Decarboxyl-2-acetylthiomethyl | 0.1% PGF2$_a$ | — | 100 | 87.5 | 87.5 | 87.5 | 50 |

*p <0.05
**p <0.01
n = 6–8

TABLE II

| PROSTANOID | (DOSE %) | EFFECT ON INTRAOCULAR PRESSURE (mmHg) Changes At AT PREDETFRMINED TIMES (HR) AFTER PG ADMINISTRATION | | | | |
|---|---|---|---|---|---|---|
| | | 1 | 2 | 3 | 4 | 6 |
| 2-Decarboxyl-2-thiomethyl-PGF2$_a$ | 0.1% | −0.5 | −1.8 | −2.8 | −1.7 | −0.2 |
| Decarboxyl-2-thiomethyl-PGF2$_a$ | 1.0% | +3.7 | +0.8 | +0.25 | +0.24 | −0.74 |

The test results clearly indicate that whereas 2-decarboxyl-2-thiomethyl-PGF$_{2\alpha}$ is essentially ineffective in lowering intraocular pressure, the corresponding acetylthiomethyyl compound is a very potent ocular hypotensive agent. The incidence of ocular surface hyperemia observed after administration of the acetylthiomethyl compound was substantially reduced, especially in the lower dose tested. This favourable separation between the ocular hypotensive activity and ocular surface hyperemia causing side effect is of great importance for the successful clinical application of these compounds in the management of glaucoma.

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

I claim:

1. A pharmaceutical composition for the treatment of ocular hypertension, comprising an amount sufficient to treat ocular hypertension of a compound of formula (III), wherein R is an acyl group derived from an alkylcarboxylic acid having from 1 to 6 carbon atoms in the alkyl moiety, and both $R_4$ and $R_5$ are hydrogen.

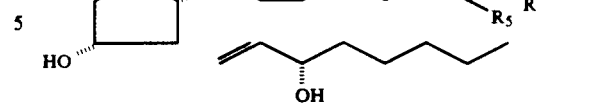

Formula III

2. The composition according to claim 1, in which in said compound of formula (III) R is acetyl, and $R_4$ and $R_5$ are hydrogen, 2-decarboxyl-2-acetylthiomethyl $PGF_{2\alpha}$.

3. A method of treating ocular hypertension, which comprises applying to the eye an amount sufficient to treat ocular hypertension of a compound of formula (III), wherein R is an acyl group derived from an alkylcarboxylic acid having from 1 to 6 carbon atoms in the alkyl moiety, and both $R_4$ and $R_5$ are hydrogen.

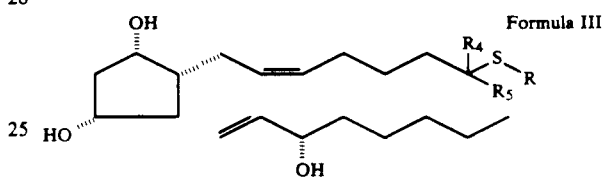

Formula III

4. A method according to claim 3 in which in said compound of formula (III) R is acetyl, and R4 and R5 are hydrogen.

* * * * *